(12) United States Patent
Berner et al.

(10) Patent No.: US 9,649,407 B2
(45) Date of Patent: May 16, 2017

(54) BODY MADE OF A CERAMIC MATERIAL

(75) Inventors: Simon Berner, Basel (CH); Joachim Bibus, Basel (CH); Heiner Bieli, Basel (CH); Alain Kounga, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 14/124,627

(22) PCT Filed: Jun. 22, 2012

(86) PCT No.: PCT/EP2012/002646
§ 371 (c)(1),
(2), (4) Date: Feb. 4, 2014

(87) PCT Pub. No.: WO2012/175218
PCT Pub. Date: Dec. 27, 2012

(65) Prior Publication Data
US 2014/0141201 A1    May 22, 2014

(30) Foreign Application Priority Data
Jun. 24, 2011 (EP) .................................. 11005172

(51) Int. Cl.
*A61L 27/30* (2006.01)
*A61L 27/10* (2006.01)
(Continued)

(52) U.S. Cl.
CPC .......... *A61L 27/306* (2013.01); *A61C 13/083* (2013.01); *A61L 27/10* (2013.01); *A61L 27/30* (2013.01); *A61L 27/50* (2013.01); *C04B 35/488* (2013.01); *C04B 41/009* (2013.01); *C04B 41/5007* (2013.01); *C04B 41/5042* (2013.01);
(Continued)

(58) Field of Classification Search
CPC .... A61L 27/306; A61L 2400/18; A61L 27/10; A61L 27/50; A61L 2430/12; A61L 27/30; A61C 13/083; A61C 8/0013; A61C 8/0015; C04B 41/5042; C04B 35/48;
(Continued)

(56) References Cited

U.S. PATENT DOCUMENTS 3,919,723 A    11/1975 Heimke et al.
2006/0084035 A1*  4/2006 Volz ..................... A61C 8/0012
                                                            433/173
(Continued)

FOREIGN PATENT DOCUMENTS

EP    2191850 A1    6/2010
ES    2352635 B1    9/2010
(Continued)

OTHER PUBLICATIONS

Integral. Dictionary.com. Retrieved Dec. 15, 2015 from http://dictionary.reference.com/browse/integral.*
(Continued)

*Primary Examiner* — Laura Auer
(74) *Attorney, Agent, or Firm* — Oliff PLC

(57) ABSTRACT

Body made of a ceramic material, the body having as an integral part thereof a surface region reaching from the surface of the body down to a predetermined depth. According to the invention, the surface region is enriched with a calcium component thereby forming a hydrophilic surface area.

22 Claims, 5 Drawing Sheets

(51) Int. Cl.
    *A61L 27/50* (2006.01)
    *A61C 13/083* (2006.01)
    *C04B 41/85* (2006.01)
    *C04B 41/87* (2006.01)
    *C04B 41/00* (2006.01)
    *C04B 41/50* (2006.01)
    *C04B 35/488* (2006.01)

(52) U.S. Cl.
    CPC .............. *C04B 41/85* (2013.01); *C04B 41/87* (2013.01); *A61L 2420/02* (2013.01); *C04B 2235/3208* (2013.01); *C04B 2235/442* (2013.01); *C04B 2235/443* (2013.01); *C04B 2235/75* (2013.01); *C04B 2235/76* (2013.01); *C04B 2235/762* (2013.01); *C04B 2235/963* (2013.01); *C04B 2235/9669* (2013.01); *Y10T 428/24355* (2015.01); *Y10T 428/265* (2015.01)

(58) Field of Classification Search
    CPC ..... C04B 2235/3208; Y10T 428/24355; Y10T 428/265
    USPC ...................... 428/141, 336, 701; 433/201.1; 623/23.57, 23.6
    See application file for complete search history.

(56) References Cited

U.S. PATENT DOCUMENTS

| | | | |
|---|---|---|---|
| 2006/0246399 A1* | 11/2006 | Ehrl ..................... | A61C 8/0012 433/201.1 |
| 2007/0184299 A1* | 8/2007 | Wei ....................... | A61L 27/306 428/689 |
| 2009/0118114 A1* | 5/2009 | Zhang et al. ................. | 501/135 |
| 2009/0191280 A1 | 7/2009 | Kokubo et al. | |
| 2009/0191507 A1 | 7/2009 | Charlton et al. | |
| 2010/0274361 A1* | 10/2010 | Ortega Cruz et al. ..... | 623/23.56 |
| 2012/0071986 A1 | 3/2012 | Anitua Aldecoa et al. | |

FOREIGN PATENT DOCUMENTS

| | | |
|---|---|---|
| JP | H02-114960 A | 4/1990 |
| JP | 2003-512895 A | 4/2003 |
| JP | 2004-075532 A | 3/2004 |
| WO | WO2008098976 A2 | 8/2008 |

OTHER PUBLICATIONS

International Preliminary Report and Written Opinion of the International Searching Authority in corresponding PCT/EP2012/002646 issued Dec. 24, 2013.

"Enhancing Surface Free Energy and Hydrophilicity through Chemical Modification of Microstructured Titanium Implant Surfaces", F. Rupp, L. Scheideler, N. Olshanska, M. de Wild, M. Wieland, J. Geis-Gerstorfer, Dept. of Prosthetic Dentistry, Nov. 3, 2005, pp. 323-334.

"Improved Osseointegration of a Novel, Hydrophilic Ti Surface—a review", Verbesserte Osseointegration einer neuen, hydrophilen Ti-Oberflache—ein Review, A. Molenberg, F. Schwarz, M. Herten, S. Berner, M. de Wild, M. Wieland, 2009 Wiley-VCH Verlag GmbH & Co. KgaA Weinheim, pp. 31-35.

* cited by examiner

All parameters surface influence (fold change)

Ca-ZrO2: ~1.15
ZrO2 Reference: ~1.0

Fig. 4

BODY MADE OF A CERAMIC MATERIAL

FIELD OF THE INVENTION

The present invention relates to a body made of a ceramic material, to a method for improving the hydrophilicity of a body made of a ceramic material, and to the use of the ceramic body as an implant, in particular as a dental implant, or as an abutment for such an implant.

BACKGROUND

Implants, such as dental implants, are well known in the art, e.g., U.S. Pat. No. 5,368,483 (Sutter), U.S. Pat. No. 8,029,283 (Schwarz) and US 2010/0068674 (Zucker) incorporated by reference herein.

Dental implants generally comprise an anchoring part, which is designed to be anchored in the jaw bone, and a mounting part, which serves as a base for the direct or indirect attachment of a suprastructure, such as a crown or bridge.

There are one-part dental implant systems, in which the anchoring part and the mounting part are integrally formed of one piece, and two-part dental implant systems, comprising a separate piece, the so-called "abutment", serving as a mounting part.

An abutment is thus a separate mounting part for a dental implant, intended for connecting the part that is anchored in the bone to the suprastructure.

Dental implants generally consist of a material, which is biocompatible and which additionally has favourable mechanical properties.

With regard to the anchoring part, it is required that the dental implant provides good osteointegration.

The term "osteointegration" designates the direct structural and functional connection between living bone and the surface of the load-bearing implant. A good osteointegration means that the implant, after reaching a primary stability by screwing it into the bone, safely ossifies within a short healing time so that a permanent bond between implant and bone is obtained.

Suitable materials for an implant are in general made of a metal, e.g. titanium, or a ceramic, e.g. a zirconium based ceramic.

In contrast to titanium implants, which are dark and therefore mismatch with the colour of natural teeth, ceramic materials have the advantage that their colour can be closely matched to the colour of natural teeth. Efforts have thus been made to provide dental implants, of which at least the parts that are visible after insertion are made of a ceramic material.

Despite these favourable properties, the use of ceramic materials for dental implants is quite often limited by their fatigue stability, which is generally rather low.

A ceramic material with sufficient mechanical stability is disclosed in U.S. Pat. No. 6,165,925. This material is, however, per se not osteointegrative.

Osteointegration has been turned out to be particularly efficient if mechanical roughening of the implant's surface is combined with subsequent etching of the roughened surface. In this regard, EP-A-1 982 670 discloses a process wherein at least a part of the surface is etched with a solution comprising hydrofluoric acid.

However, a further improvement of the osteointegrative properties of the implant is still the subject of on-going research, since it allows a permanent bond between implant and bone to be established in a relatively fast manner, ultimately allowing a shortening of the healing time after the implantation.

SUMMARY OF THE INVENTION

The object of the present invention is thus to provide a ceramic body having improved hydrophilicity.

The present invention thus relates to a body made of ceramic material, the body comprising as an integral part thereof a surface region reaching from the surface down to a predetermined depth. According to the invention, said surface region is enriched with a calcium component thereby forming a hydrophilic surface area.

Given the fact that the surface region reaches down to a predetermined depth, the body further comprises—as a "remainder"—a core region, which is enclosed by said surface region. Since the surface region is an integral part of the body, the surface region and the core region are formed integrally.

In general, the term "enriched" as used in the context of the present invention relates to the surface region of the ceramic body comprising a higher proportion of the calcium component than the remainder, i.e. the core region, of the body. The term "proportion" as used in this context relates to the molar percentage of calcium in any form, (in particular ionic form), relative to the total number of atoms or molecules, respectively, of the ceramic material.

As will be shown below, the enrichment in the calcium component is in general achieved by incorporation of the calcium component into the ceramic body due to diffusion or permeation. According to a preferred embodiment, the calcium component is thus integrated in the ceramic material of the surface region. As will be discussed below, the calcium component is preferably calcium ions or calcium oxide (CaO).

Specifically, the body according to the present invention is used as an implant, more specifically as a dental implant.

It has surprisingly been found that the ceramic body of the present invention allows an implant or abutment to be obtained with an improved hydrophilicity. It has also been found that the hydrophilicity achieved according to the present invention is stable; particularly, the hydrophilicity is maintained during storage of the body in aqueous solution.

It has further been found that this improvement of the hydrophilicity goes along with improved osteointegrative properties of the ceramic surface. This renders the body of the present invention particularly suitable for the use as a dental implant or abutment.

The improved hydrophilicity is not only beneficial on the implant's anchoring part, but also on its mounting part (or a respective intermediate part, respectively) in view of an improved interaction between the implant or abutment and the surrounding soft tissue.

Specifically, the term "hydrophilic" or "hydrophilicity" as used in the context of the present invention refers to a contact angle of the hydrophilic surface area being less than 90°, more preferably less than 30°, most preferably less than 10°.

Without wanting to be bound by the theory, hydrophilicity of the surface playing a crucial role in the osteointegration process can partly be explained by the fact that it goes along with an improved attachment of certain proteins (e.g. fibrinogen, plasma fibronectin) and the resulting stabilization of the blood clot. This finally results in the faster formation of new bone.

Aiming at a fast healing process, which includes preventing acute or chronic inflammatory processes, the present invention thus allows a quick and mechanically stable osteointegration due to an intimate contact of the implant with the surrounding bone tissue structure.

Considering the fact calcium embodies an essential component in the formation of bone structures, ceramic body of the present invention further promises to have positive effect on bone growth for the reason that the calcium component enriched surface region can serve as a nutrient source for the osteoblasts.

According to a preferred embodiment of the present invention, the ceramic material of the body of the present invention comprises zirconia. Zirconia ceramic shows no interactions with other dental materials and is electrically neutral. Because of a friendly gum reaction and due to findings that dental plaque seems to be less attached to this material, it bears a very low risk of inflammation. In addition, the material has a light colour and can thus be closely adapted to natural tooth colour.

According to a most preferred embodiment the implant according to the present invention is made of ceramic comprising an yttria-stabilized zirconia. In general, the yttria-stabilized zirconia used is tetragonal in phase. Yttria-stabilized tetragonal zirconia has a very high strength, a high toughness and a good wear resistance.

Apart from yttria-stabilized zirconia, also e.g. alumina-stabilized zirconia or ceria-stabilized zirconia can be used for the present invention. Other ceramic materials, such as zirconia-stabilized alumina, are thinkable. In this regard, the term "ceramic material" is to be understood to also include glass ceramic materials.

According to a further preferred embodiment of the present invention, the ceramic material comprises in the surface region at least a calcium containing crystalline phase. It is further preferred that this calcium containing crystalline phase is solely present in the surface region, meaning that it is absent in the remainder, e.g. the core region, of the body.

When the material comprises zirconia, it is particularly preferred that a phase of the system Ca—Zr—O, i.e. a crystalline phase containing calcium, zirconium and oxygen, is present.

In particular, the calcium containing crystalline phase can be a phase of the system $CaO$—$ZrO_2$ and, more particularly, is selected from the group consisting of a monoclinic $CaZr_4O_9$ phase, a cubic $CaZrO_3$ phase and an orthorhombic $CaZrO_3$ phase. It is thereby particularly preferred that the calcium containing crystalline phase is an orthorhombic $CaZrO_3$ phase.

For an orthorhombic $CaZrO_3$ phase to be formed, a relatively high amount of calcium or its oxide, respectively, in the surface region is required.

In this regard, it is preferred that the amount of CaO in the surface region preferably ranges from about 3 mol-% to about 50 mol-%, more preferably from about 6 mol-% to about 50 mol-%, and most preferably from about 15 mol-% to about 30 mol-%. In this context, mol-% refers to the number of CaO versus the sum of CaO and $ZrO_2$ of the material of the surface region.

In view of achieving a high hydrophilicity without interfering with the intrinsic properties of the material, it is preferred that the surface region reaches from the surface of the body down to a depth of about 10 μm at most, more preferably of about 1 μm at most, even more preferably of about 500 nm at most, and most preferably of about 200 nm at most. Within this range, the surface region is thought to be sufficiently thin in order to preserve intrinsic properties of the ceramic material and its surface topography while improving hydrophilicity. Thus, apart from an improved hydrophilicity, the other properties of the ceramic material—e.g. the visual appearance of the body—can be kept essentially unchanged. Also the mechanical properties of ceramics, thus the strength, toughness and wear resistance of e.g. yttria-stabilized tetragonal zirconia can be maintained.

However, it may also be preferred that the surface region reaches from the surface of the body down to a depth of about 10 nm at least, more preferably about 50 nm at least, and even more preferably of about 200 nm at least.

It has been found that when providing a surface region extending to this depth, not only an improved hydrophilicity is achieved, but that the body also shows an improved resistance to hydrothermal aging.

This is of particular importance with regard to the use of a ceramic material, in particular a zirconia ceramic material, as a dental implant, since a dental implant is particularly prone to aging due to its surrounding after implantation. With regard to dental implants, the problem is aggravated by the fact that they are often subjected to a subtractive treatment, in particular an etching process, in order for roughening the surface and thus render it more osteointegrative. Etching, however, usually promotes hydrothermal aging. According to the present invention, the detrimental hydrothermal aging effects can be reduced or eliminated, even in the case that the body is subjected to etching (or another subtractive roughening treatment.)

According to a further preferred embodiment of the invention, the proportion of the calcium component typically increases continuously from the predetermined depth towards the surface of the body. In other words, there is in the surface region, thus, a gradient of the calcium component decreasing from the surface towards the core region. This is a consequence of the straightforward method of the present invention which will be disclosed in detail below. As a result, the proportion of the calcium component is highest where it is a major importance for providing hydrophilicity.

According to a further preferred embodiment of the invention, the hydrophilic surface area is formed at least on the portion of the body which is intended to be in contact with bone tissue, since in this portion the improved hydrophilicity is of particular importance.

Alternatively or additionally, it is also thinkable that the hydrophilic surface area is formed at least on the portion of the body that is intended to be in contact with the soft tissue, as it has been found that also the attachment of soft tissue to the implant can be improved by a higher hydrophilicity, although the underlying mechanisms are assumed to be different than the mechanisms leading to improved osteointegration.

According to a specifically preferred embodiment, the hydrophilic surface area is formed on the entire surface of the body. As mentioned above, it is also thinkable that the hydrophilic surface area is formed only on a part of the body.

It is further preferred that at least a part of the hydrophilic surface area has a surface roughness, in particular a combination of microscopic and macroscopic roughness, as obtainable by the process as described by EP-A-1982671 according to EP-A-1982670. A detailed description for providing microscopic roughness is found in EP-A-1982670, in particular paragraphs [0024] to [0030], [0060] to [0064] and [0079] to [0081], the disclosure of which is hereby incorporated by reference.

The described combination of microscopic and macroscopic surface roughness further contributes to high osteointegrative properties of the implant.

In addition to the body described above, the present invention further relates to a method for improving the hydrophilicity of a body. The method comprises the subsequent steps of a) applying at least one calcium compound selected from the group consisting of a calcium salt (including those salts comprising anions that are instable, e.g. against temperature, water, air, etc.; like $Ca(HCO_3)_2$)), calcium oxide, calcium hydroxide, metallic calcium and a calcium containing gel onto the surface of a basic ceramic body;

b) thermally treating the basic ceramic body with the calcium compound applied thereon at a temperature higher than 200° C., whereby a calcium component based on the calcium compound diffuses into the ceramic material. Thereby, a stable bond of the calcium component and the ceramic body is formed in a sense that rinsing with aqueous solution does not remove the calcium component.

The temperature of heat treatment b) is preferably set above the decomposition temperature of the calcium compound. Typically, the temperature of heat treatment b) is lying in the range of about 600° C. to about 1650° C., preferably about 600° C. to about 900° C.

It is understood that the temperature is also dependent on the respective ceramic material of the basic body. For example, for a material of the type Tosoh or MZ111, which are known to a skilled person, as well as for a pre-sintered basic body, the temperature of the thermal treatment b) might be different. The temperature of the thermal treatment preferably ranges from about 250° C. to about 1650° C., more preferably from about 900° C. to about 1500° C., and most preferably from about 950° C. to about 1350° C.

In the context of the present invention the term "calcium compound" is used for the calcium species applied onto the ceramic body, whereas the term "calcium component" is used for the calcium species that diffuses into the ceramic body and is thereby integrated in the surface region of the body.

Since calcium ions or CaO is the preferred component to diffuse into the ceramic body, the calcium compound to be applied onto the surface of the basic ceramic body is preferably a compound which in the course of the thermal treatment forms CaO. Further, calcium ions are likewise preferred to diffuse into the ceramic body. According to a particularly preferred embodiment, a calcium salt selected from the group of $Ca(HCO_3)_2$, $CaCO_3$ and $Ca(NO_3)_2$ is used.

The application of the calcium compound, such as CaO, $Ca(OH)_2$, $Ca(HCO_3)_2$, $Ca(NO_3)_2$, $CaCO_3$, Ca-citrate or Ca-acetate, can be carried out by e.g. soaking/immersion, dipping or drop casting, by embedding into powder, e.g. when using $CaCO_3$, by the use of spin coating, electrophoresis, sandblasting, or by plasma immersion ion implantation (PIII).

It has been found that by applying a calcium containing gel or paste, e.g. a $CaCO_3$ containing paste, a particularly high amount of calcium diffusing into the body can be achieved. The application of a calcium containing gel is particularly preferred, since thereby the formation of a $CaZrO_3$ phase, more particularly an orthorhombic $CaZrO_3$ phase, in the surface region of the body can be achieved. In this embodiment, the proportion of monoclinic phase in the surface region is very low, if not 0, and a very high hydrothermal stability is achieved. As will be shown by way of the examples, the application of a calcium containing gel allows a very high hydrothermal stability to be achieved even if the basic ceramic body has been subjected to a sand-blasting and etching treatment.

Alternatively to the method described above, other methods for the application of the calcium compound include the application of a calcium containing gel, physical vapour deposition (PVD), chemical vapour deposition (CVD) and atomic layer deposition (ALD).

Given the fact that the calcium component diffuses into the ceramic material, there is no discrete coating and thus no discrete boundary between the calcium component and the basic body. Consequently, there is no splitting or washing off of the calcium component, as it is typically seen when a separate coating of an additional material is applied on a ceramic body.

The method of the present invention allows thus a calcium component to be integrated into the body in a very simple manner. The calcium component being integrated into the material of the body is in clean contrast to the teaching of EP-A-1847278, relating to titanium and thus to a material for which a diffusion of a calcium component by the thermal treatment according to step b) would not be obtained.

The actual temperature to achieve a sufficient diffusion of the calcium component into the ceramic material depends on the specific ceramic material and the calcium compound used. As mentioned, calcium ions and/or CaO are the preferred components to diffuse and integrate into the ceramic body.

The depth of diffusion of the calcium component can be adjusted by appropriately setting the temperature and the duration of the thermal treatment according to step b). A skilled person who has become aware of the teaching of the present invention knows how to set these parameters in order to achieve the desired depth of diffusion.

If apart from a high hydrophilicity also a high hydrothermal stability is to be achieved, the temperature for the heat treatment is preferably in the range from about 500° C. to about 1650° C., more preferably from about 900° C. to about 1500° C., and most preferably from about 950° C. to about 1350° C. This allows a depth of diffusion of more than 1 µm to be achieved. As mentioned above, a corresponding ceramic body not only has a highly hydrophilic surface, but also shows an improved resistance to hydrothermal aging.

In general, the body of the present invention is prepared using a sintering process. It is in this regard thinkable that method step a), i.e. the application of the calcium compound, is performed on the (pre-sintered) white body, which is afterwards subjected to the final sintering temperature and thus simultaneously also to the thermal treatment according to step b).

This process is particularly suitable if the body's resistance to hydrothermal aging is to be improved.

According to a particularly preferred embodiment, a zirconia ceramic body is pre-sintered at about 1350° C. for about 2 hours, then covered with a $CaCO_3$ powder followed by final sintering at about 1450° C. for about 2 hours.

According to a further preferred embodiment of the invention, the thermal treatment is followed by cleaning the dental implant of non-specifically bonded, residual calcium compound. This cleaning step is preferably performed by rinsing the dental implant with pure water or an aqueous solution like e.g. NaCl solution, or another liquid. In particular if the calcium compound applied is in solid form, e.g. as $CaCO_3$ powder, other cleaning methods, such as air streaming, brushing and/or polishing can be performed for the removal.

The performance of the washing step can be improved by using ultrasound. Thereby, grains, grain agglomerates or reaction products which loosely adhere to the surface are effectively removed.

The dental implant which has been thermally treated and subjected to the above described cleaning step has a hydrophilic surface and is biologically active.

According to a further preferred embodiment of the present invention, the process comprises the step of roughening at least a part of the surface of the basic body by a subtractive treatment before applying the calcium compound. It is in this context further preferred that the subtractive treatment comprises two sequential roughening steps: a first step for providing a macroscopic surface roughness, e.g. by a sand-blasting, prior to a second step that provides a microscopic surface roughness, e.g. acid etching. In this regard it is referred to the process according to EP-A-1982670 paragraphs [0055] to [0064], the disclosure of which is incorporated herein by reference.

In particular, the step of roughening can be performed after the final sintering step, which is carried out after application of the calcium compound on the pre-sintered white body.

As mentioned above, the object achieved by the present invention is particularly useful in the field of implantology, in particular in oral implantology. The present invention thus further relates to the use of the body as an implant, in particular a dental implant.

The present invention likewise relates to the use of the body as an abutment for such an implant. All features and advantages mentioned above for an implant, in particular a dental implant, likewise apply to an abutment.

BRIEF DESCRIPTION OF THE DRAWINGS

FIG. 4 shows a graphical representation of the fold change in the expression of a number of different parameters for Example 2c ("referred to as Ca—$ZrO_2$") and comparative Example 2d ("referred to as $ZrO_2$ Reference")

DETAILED DESCRIPTION

Figure 1:
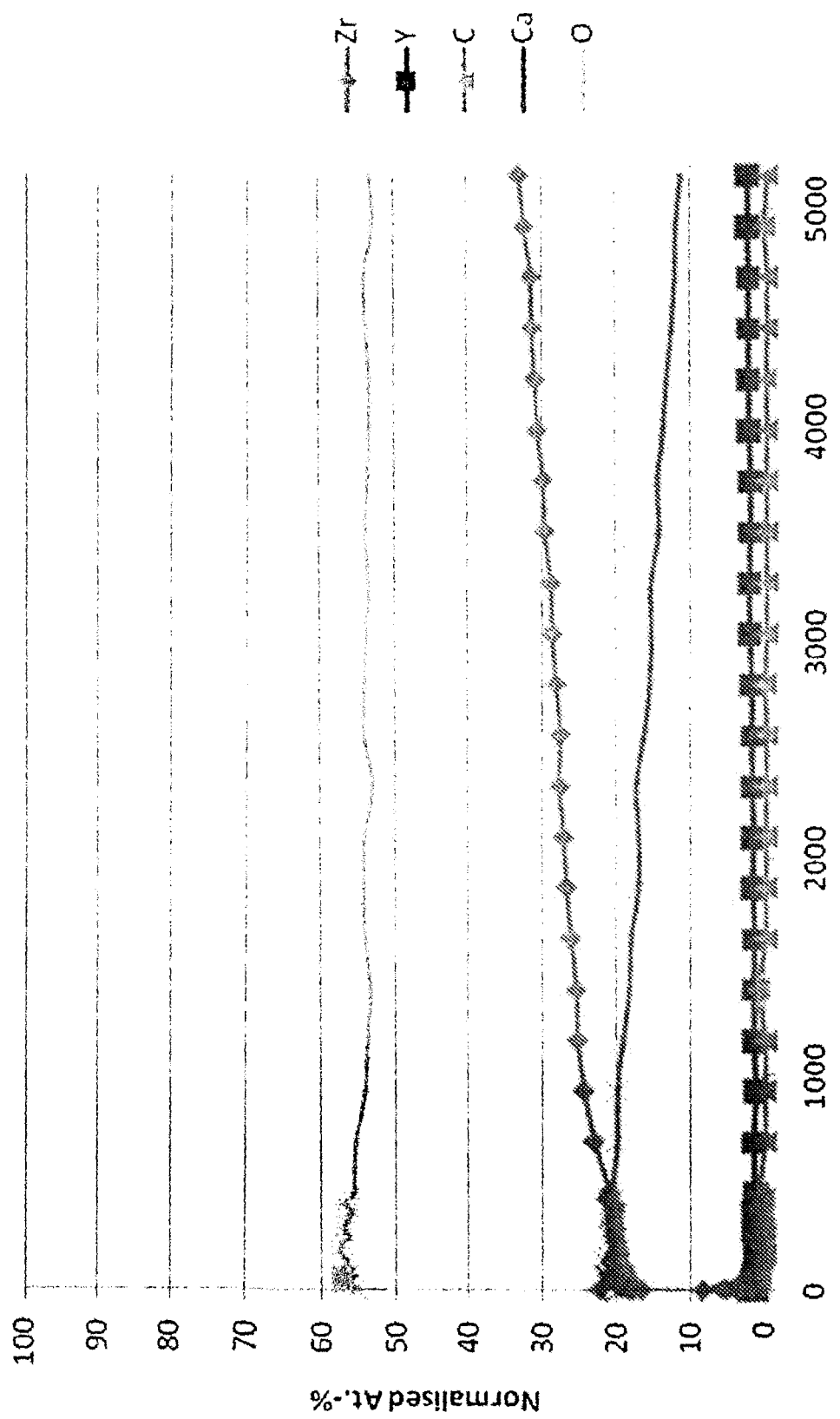
FIG. 1 shows a graphical representation of the normalized atomic concentrations of the elements (Zr, Y, C, Ca, O) comprised in the body obtained according to Example 4a in relation to the depth of the body.

The present invention is further illustrated by way of the following examples:

EXAMPLE 1

Method for Preparing a Ceramic Body Comprising a Calcium Component Enriched Surface Region by Immersion in $Ca(OH)_2$ A solution of 0.02 M $Ca(OH)_2$ in water was prepared (1480 mg/l).

Preparation of Samples

Smooth $ZrO_2$ discs (Tosoh) with a diameter of 14 mm having a smooth, polished surface were cleaned with a basic, phosphate-free cleaning agent (Deconex 15PF from Max F. Keller GmbH, Mannheim), subjected to ultra sonication for 5 min and to standard oxygen plasma cleaning (using an apparatus of the type "Femto" by Diener Electronics GmbH+Co. KG, Ebhausen, Germany; 35 W, 6 sccm ("standard cubic centimeter per minute"; 1 $cm^3$ per minute at normal pressure, i.e. 1013 mbar), $O_2$ gas flow, p≈0.1 mbar, time=2.5 minutes).

The cleaned discs were immersed in the 0.02 M $Ca(OH)_2$ solution in glass test tubes (about 10 ml) and then—still completely wet—subjected to a thermal treatment at 650° C. for 2 hours in a high temperature oven. This treatment resulted in the formation of strongly hygroscopic CaO.

The discs were cooled down in the high temperature oven under $N_2$ or air. The discs were then removed from the oven and immersed in water. In a strongly exothermic reaction of CaO and $H_2O$, $Ca(OH)_2$ was thereby formed, which further reacts with $CO_2$ into $CaCO_3$.

The treated discs were then rinsed with ultrapure water according to the following procedure: Two glass beakers were filled with water (about 300 ml each) and the discs were immersed for about 5 seconds in each of the beakers while performing slow swirling movements.

The discs were then removed from the glass beakers and the surface was dried under a stream of argon.

Contact Angles (CA)

For three samples, the contact angles were determined using pure water according to the sessile drop method (EasyDrop DSA20 E, Krüss GmbH). For the more hydrophilic samples, a drop size of 0.3 µl was chosen and for the less hydrophilic samples, a drop size of 3.0 µl was chosen, respectively. The contact angles were calculated by fitting a circular segment function to the contour of the droplet placed on the surface.

The results of the contact angles as a function of the exposure time to laboratory air are represented below:

| Storage time [weeks] | CA [°] of Sample 1.1 | CA [°] of Sample 1.2 | CA [°] of Sample 1.3 |
| --- | --- | --- | --- |
| 0 | 0.0 | 0.0 | 0.0 |
| 2 | 22.8 | 31.8 | 34.7 |
| 4 | 31.6 | 42.3 | 40.4 |
| 9 | 40.7 | 38.9 | 39.9 |

Surface Composition

For two samples, the chemical composition of the surface was determined by XPS and is represented below:

| # | Zr [%] | Y [%] | C [%] | K [%] | O [%] | Si [%] | Na [%] | Al [%] | Ca [%] |
| --- | --- | --- | --- | --- | --- | --- | --- | --- | --- |
| 1.1 | 20.1 | 1.2 | 13.0 | 0.1 | 53.4 | 1.9 | 0.1 | 0.8 | 8.4 |
| 1.2 | 16.8 | 1.1 | 15.5 | 0.0 | 53.5 | 1.2 | 0.2 | 0.4 | 9.9 |

EXAMPLE 2

Method for Preparing a Ceramic Body Comprising a Calcium Component Enriched Surface Region Using $Ca(HCO_3)_2$ and Temperatures from 950 to 1200° C.

A solution of 0.02 M $Ca(HCO_3)_2$ in water was prepared according the following procedure: a 0.02 M $Ca(OH)_2$ solution was prepared and sterile filtrated in order to separate insoluble $CaCO_3$ contamination from the $Ca(OH)_2$ solution. $CO_2$ was fed into the solution until the initially turbid solution (due to the presence of $CaCO_3$) became clear again.

Preparation of Samples

Smooth $ZrO_2$ discs (Tosoh) with a diameter of 14 mm having a smooth, polished surface were cleaned, sonicated and subjected to standard oxygen plasma cleaning according to the procedures described in Example 1. 100 μl of the 0.02 M $Ca(HCO_3)_2$ solution was placed onto the discs using a pipette before they were thermally treated in the high temperature oven at 950° C. (2a) or 1200° C. (2b), respectively. This resulted first in the formation of $CaCO_3$ which further reacted to CaO and $CO_2$ at these temperatures.

The discs were then removed from the high temperature oven and then cooled down under air. The discs were then rinsed with ultrapure water according to the procedure described in Example 1 and blown dry under a stream of argon.

For an in vitro analysis, further samples have been prepared according to the treatment of 2a and 2b but with the difference that sand-blasted and acid etched $ZrO_2$ discs (of the material MZ111 and having a diameter of 5 mm) have been used and that the heat treatment was at 1150° C. for 2 hours (Example 2c).

Further, a reference Example 2d was prepared in analogy to Example 2c, but without applying a $Ca(HCO_3)_2$ solution onto the discs and without thermal treatment. Sample 2c has been stored in NaCl solution and sterilized using an autoclave (121° C., 20 minutes), whereas sample 2d has been sterilized using an $H_2O_2$ plasma.

Contact Angles (CA)

For Example 2a, the contact angles of three samples were determined and calculated according to the described methods in Example 1.

The results for the samples are represented below:

| Storage time [weeks] | CA [°] of Sample 2a.1 | CA [°] of Sample 2a.2 | CA [°] of Sample 2a.3 |
|---|---|---|---|
| 0 | 3.8 | 0 | 0 |
| 1 | 22.4 | 22.3 | 24.5 |
| 4 | 56.6 | 48.7 | 44.6 |
| 6 | 59.3 | 61.2 | 47.4 |

Surface Composition

The chemical composition of the surface was determined by XPS. The average values of two measurements per example are represented below:

| # | Zr [%] | Y [%] | C [%] | O [%] | Si [%] | Al [%] | Ca [%] |
|---|---|---|---|---|---|---|---|
| 2a | 15.0 | 1.0 | 17.8 | 52.4 | 2.1 | 0.4 | 11.3 |
| 2b | 17.3 | 1.0 | 20.9 | 47.2 | 1.8 | 2.0 | 9.7 |

EXAMPLE 3

Method for Preparing a Ceramic Body Comprising a Calcium Component Enriched Surface Region Using $CaCO_3$ Preparation of Samples Smooth $ZrO_2$ discs (Tosoh) with a diameter of 14 mm having a smooth, polished surface were cleaned with a basic, phosphate-free cleaning agent (Deconex 15PF from Max F. Keller GmbH, Mannheim) and subjected to ultra sonication for 5 min and to oxygen plasma cleaning (using an apparatus of the type "Femto" by Diener Electronics GmbH+Co. KG, Ebhausen, Germany; 35 W, 6 sccm ("standard cubic centimeter per minute"; 1 $cm^3$ per minute at normal pressure, i.e. 1013 mbar), $O_2$ gas flow, p≈0.1 mbar, time=2.5 minutes).

The discs were then covered with $CaCO_3$ powder by putting the discs into an $Al_2O_3$ dish and the $CaCO_3$ powder was sprinkled onto them through a sieve (about 15 mg per disc).

The samples were thermally treated in the high temperature oven:

Example 3a; 780° C. for 2 h

Example 3b; 950° C. for 2 h

Example 3c; 950° C. for 16 h

Powder residues were then brushed off the treated discs before rinsing them with ultrapure water according to the procedure described in Example 1.

The discs were dried under a stream of argon.

Contact Angles (CA)

The contact angles for samples 3a and 3b were determined and calculated according to the described methods in Example 1.

The results of three measurements per Example 3a and 3b are represented below:

EXAMPLE 3a

| Storage time [weeks] | CA [°] of Sample 3a.1 | CA [°] of Sample 3a.2 | CA [°] of Sample 3a.3 |
|---|---|---|---|
| 0 | 0.0 | 0.0 | 0.0 |
| 2 | 26.3 | 23.0 | 38.2 |
| 4 | 34.0 | 34.1 | 43.8 |
| 6 | — | 39.2 | 53.6 |

EXAMPLE 3b

| Storage time [weeks] | CA [°] of Sample 3b.1 | CA [°] of Sample 3b.2 | CA [°] of Sample 3b.3 |
|---|---|---|---|
| 0 | 0.0 | 0.0 | 0.0 |
| 2 | 34.9 | 43.8 | 38.6 |
| 4 | 54.2 | 60.6 | 45.7 |
| 6 | 53.6 | 48.2 | 42.0 |

Surface Composition

The chemical composition of the surface was determined by XPS. The average values of two measurements for each Sample 3a, 3b and 3c are represented below:

| # | Zr [%] | Y [%] | C [%] | K [%] | O [%] | Si [%] | Na [%] | Al [%] | Ca [%] |
|---|---|---|---|---|---|---|---|---|---|
| 3a | 25.2 | 1.6 | 10.4 | 0.0 | 53.1 | 3.4 | 1.0 | 1.3 | 3.3 |
| 3b | 21.5 | 1.5 | 14.0 | 0.0 | 51.7 | 2.6 | 0.1 | 1.2 | 6.9 |
| 3c | 21.6 | 1.5 | 12.3 | — | 52.2 | 2.3 | 0.0 | 1.3 | 8.2 |

Reference Example at 950° C.:
Preparation of Samples

Smooth $ZrO_2$ discs (Tosoh) with a diameter of 14 mm having a smooth, polished surface were cleaned, subjected to ultra-sonication and rinsed with ultrapure water as a last step according to the procedures described in Example 1.

The oxygen plasma cleaned discs were subjected to a thermal treatment at 950° C. for 2 hours in the high temperature oven. The discs were then removed from the high temperature oven and let cool down under air.

The treated discs were then rinsed with ultrapure water according to the following procedure: Two glass beakers were filled with water (about 300 ml each) and the discs were immersed twice for about 5 seconds in each of the beakers while performing slow swirling movements. Then they were subjected to ultra-sonication for 5 min before repeating the rinsing step described before.

The discs were then removed from the glass beakers and the surface was dried under a stream of argon.

Contact Angles (CA)

The contact angles of three measurements per sample were determined and calculated according to the described methods in Example 1.

The results are represented below:

| Storage time [days] | CA [°] of Sample Ref_1.1 | CA [°] of Sample Ref_1.2 | CA [°] of Sample Ref_1.3 |
|---|---|---|---|
| 3 | 53.4 | 49.9 | 52.9 |
| 10 | 84.4 | 82.7 | 77.6 |
| 30 | 88.3 | 102.5 | 93.3 |
| 66 | 98.9 | 102.6 | 99.6 |

The experimental data show that an improvement in hydrophilicity was obtained upon thermal treatment of samples on which previously a calcium compound has been applied. Highly hydrophilic samples were obtained when $Ca(OH)_2$, $Ca(HCO_3)_2$ or $CaCO_3$ (powder) was used as calcium compound.

Chemical composition analysis clearly showed that all samples treated with a calcium compound display a higher proportion of calcium in their surface regions. Especially those samples that were treated at a temperature of 950° C. or 1200° C. displayed a proportion of calcium higher than 10% but a lower proportion of carbon. This underlines the theory that by the high thermal treatment, CaO is formed which diffused into the ceramic material, while gaseous $CO_2$ escaped.

This and the fact that rinsing or cleaning procedures does not have an effect on the measured calcium proportion is regarded as a clear indication that by the process of the present invention the calcium component is integrated into the ceramic body by diffusion or permeation.

EXAMPLE 4

Method Using $CaCO_3$ Application Prior to Final Sintering Step

In a further Example 4a, discs of pressed $ZrO_2$ (Tosoh-Zirconia TZ-3YSB-E) were pre-sintered at a temperature of 1350° C. for 2 hours in a sintering oven (Nabertherm; including a slow temperature increase with a holding time of 2 hours at 600° C.). The resulting pre-sintered discs were then covered with $CaCO_3$ powder by putting the discs into an $Al_2O_3$ dish and sprinkling the $CaCO_3$ powder onto them through a sieve (about 15 mg per disc). Final sintering was then carried out at 1450° C. for 2 hours.

Powder residues were then brushed off the treated discs before rinsing them with ultrapure water.

The discs were dried under a stream of argon.

Further, a reference Example 4b was prepared in analogy to Example 4a, but without covering the pre-sintered discs with $CaCO_3$ powder.

Normalized Atomic Concentration Determined by X-Ray Photoelectron Spectroscopy (XPS)

As will be shown by way of the Figures, XPS measurement of the discs according to Example 4a revealed that even at a depth of 5 μm the material has a normalized atomic concentration of calcium of more than 10% and that calcium is present even at a depth of about 10 μm.

The results can be explained by a thermally induced diffusion of calcium into the ceramic material of the basic body.

Analysis of Crystal Structure by X-Ray Diffraction (XRD)

In order to determine the crystal structure, the discs were further analysed by X-ray diffraction (XRD) using a diffractometer of the type Empyrean (PANalytical) in the θ/θ (theta/theta)-constellation (radiation source: Cu (40 kV/40 mA); range of incidence angle: 20° to 70°; step width: 0.026°; measuring time per measuring point: 300 s).

XRD measurement revealed three different phases, namely a monoclinic $CaZr_4O_9$ phase, a cubic $CaZrO_3$ phase and an orthorhombic $CaZrO_3$ phase, in the proportions given below:

| Phase | Proportion/% |
|---|---|
| $CaZr_4O_9$ (monoclinic) | 23.7 |
| $CaZrO_3$ (cubic) | 6.0 |
| $CaZrO_3$ (orthorhombic) | 70.3 |

Also, the contact angles of Example 4a were determined and calculated according to the methods as described in the context of Example 1.

EXAMPLE 5

Method Using a Calcium Containing Gel

A further sample (Example 5) has been prepared by applying a calcium containing gel on a disc (acid etched and sand-blasted) of a sintered material (MZ111).

To this end, a Ca containing gel consisting of $Ca(NO_3)_2$, PVA (polyvinyl alcohol, 22 kD molecular weight) and water was prepared. Specifically, solutions of 20 wt-% PVA and 20 wt-% $Ca(NO_3)_2*4H_2O$ were prepared with water and mixed at a ratio of 1:1.

After plasma treating the discs as specified above, the gel was applied to the discs in a thickness of about 2 mm.

The discs with the gel applied thereon were heated to 1150° C. for 2 hours, then cooled in air, rinsed with ultrapure water and dried under a stream of argon.

Also for Example 5, the normalized atomic concentration was determined by X-Ray Photoelectron Spectroscopy (XPS), as described above in the context of Example 4.

The results are discussed in the context of the figures, of which

Figure 2:
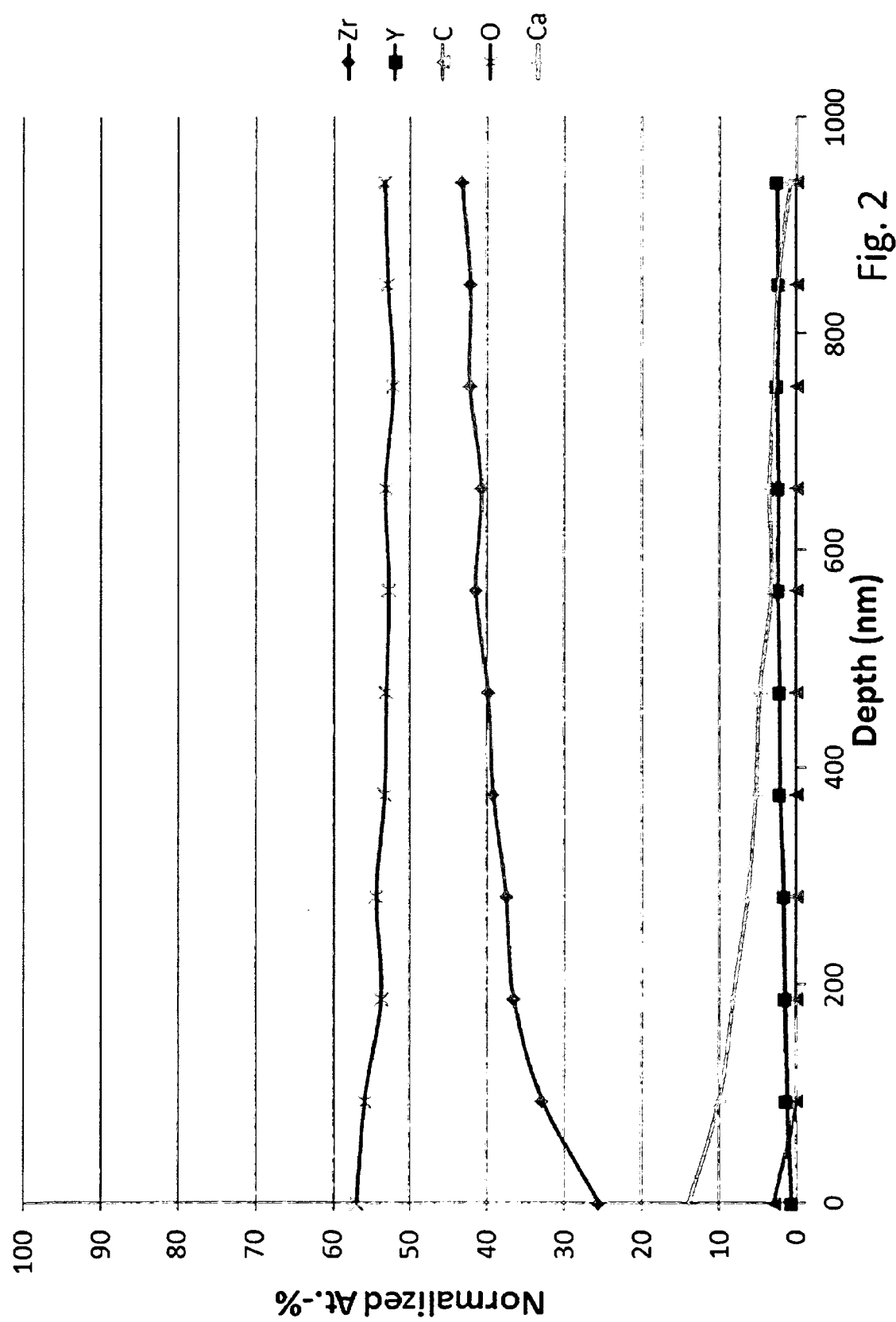
FIG. 2 shows a graphical representation of the normalized atomic concentrations of the elements (Zr, Y, C, Ca, O) comprised in the body obtained according to Example 5 in relation to the depth of the body.
Figure 3:
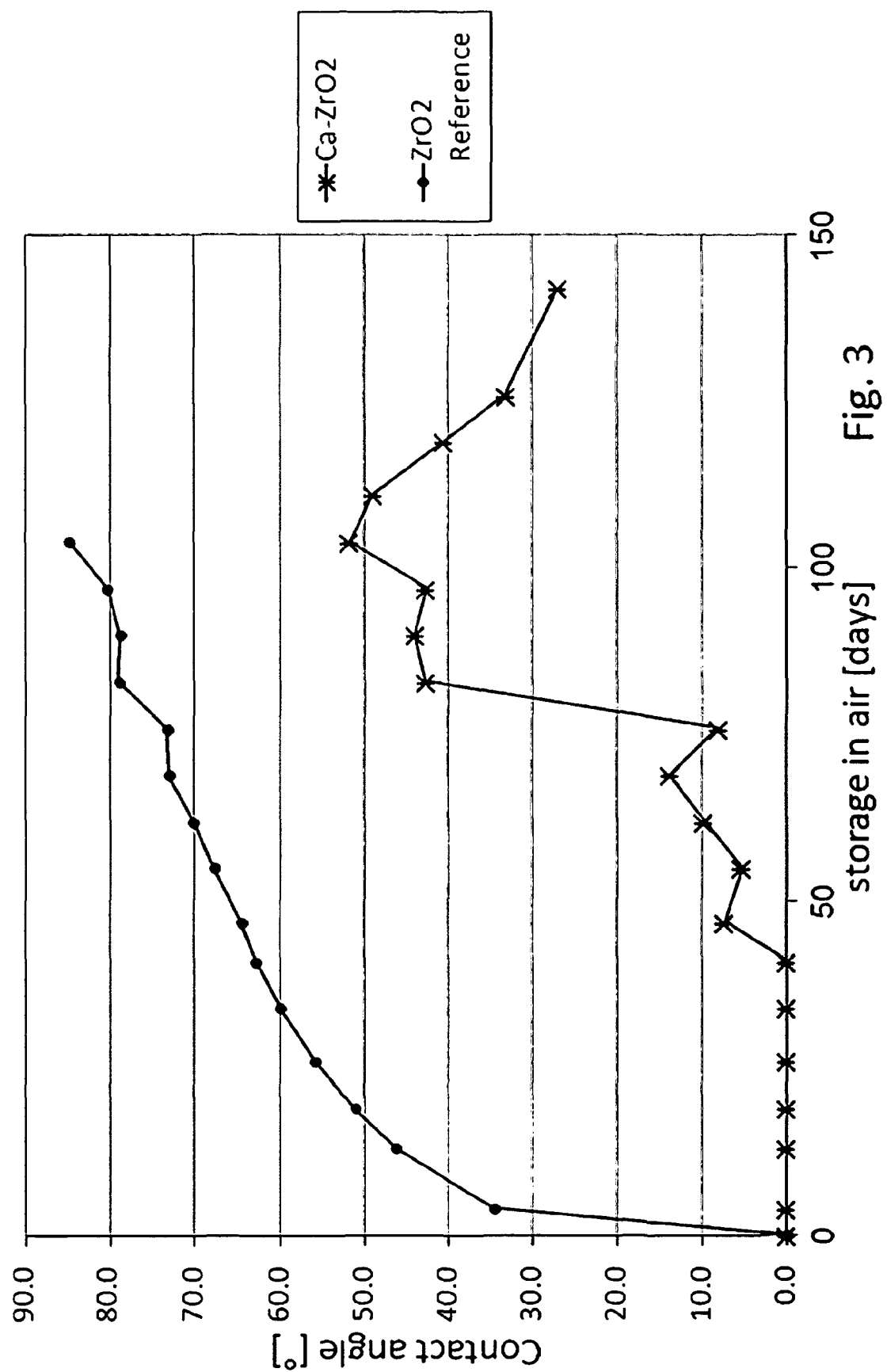
FIG. 3 shows a graphical representation of the contact angle as a function of storage time in air for Example 4a ("referred to as Ca—$ZrO_2$") in comparison to comparative Example 4b ("referred to as $ZrO_2$ Reference")
Figure 5:
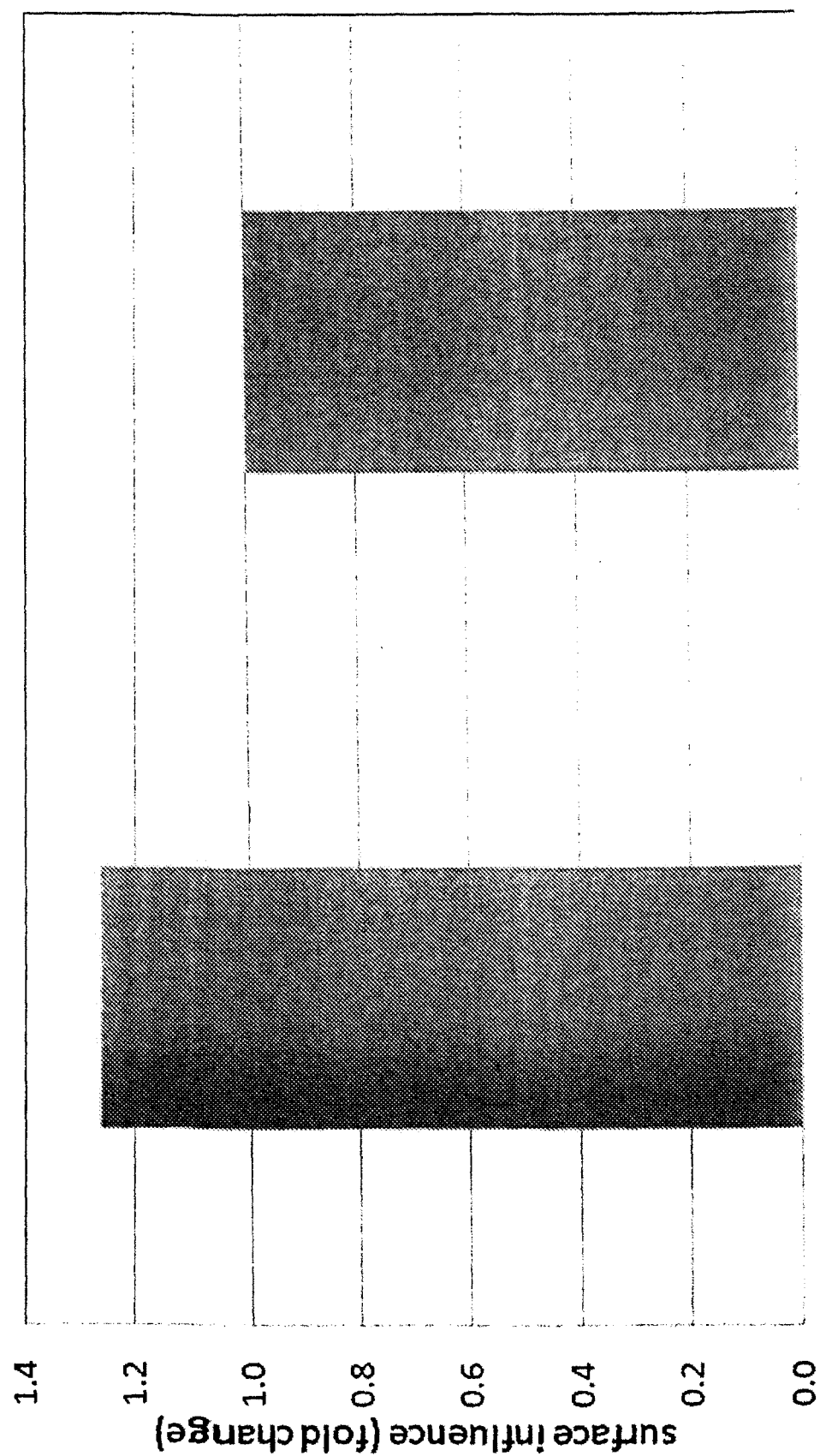
FIG. 5 shows a graphical representation of the fold change in the expression of a number of differentiation parameters indicative for bone formation for Example 2c ("referred to as Ca—$ZrO_2$") and comparative Example 2d ("referred to as $ZrO_2$ Reference").

FIG. 1 shows a graphical representation of the normalized atomic concentrations of the elements (Zr, Y, C, Ca, O) comprised in the body obtained according to Example 4a in relation to the depth of the body;

FIG. 2 shows a graphical representation of the normalized atomic concentrations of the elements (Zr, Y, C, Ca, O) comprised in the body obtained according to Example 5 in relation to the depth of the body;

FIG. 3 shows a graphical representation of the contact angle as a function of storage time in air for Example 4a ("referred to as Ca—$ZrO_2$") in comparison to comparative Example 4b ("referred to as $ZrO_2$ Reference");

FIG. 4 shows a graphical representation of the fold change in the expression of a number of different parameters for Example 2c ("referred to as Ca—$ZrO_2$") and comparative Example 2d ("referred to as $ZrO_2$ Reference"); and FIG. 5 shows a graphical representation of the fold change in the expression of a number of differentiation parameters indicative for bone formation for Example 2c ("referred to as Ca—$ZrO_2$") and comparative Example 2d ("referred to as $ZrO_2$ Reference").

As shown in FIG. 1, the material of the body according to Example 4a shows at a depth of 5 μm a normalized atomic concentration of calcium of more than 10%; by extrapolation, it can be concluded that calcium is present even at a depth of about 10 μm.

For the sample for which the calcium compound (in the form of a calcium containing gel) has been applied on a sintered basic body (Example 5), still a depth of diffusion of about 1 μm was observed, as shown in FIG. 2.

As shown in FIG. 3, Example 4a according to the present invention showed even after storage in air for 6 weeks a contact of angle of 0°, whereas for comparative Example 4b, an increase in the contact angle higher than 35° was measured after a few days of storage already. Thus, the (super-) hydrophilicity obtained according to the present invention is preserved, even after a long period of storage in air.

As further shown in FIGS. 4 and 5, respectively, the in vitro-analysis revealed for Example 2c a 1.2 fold mean change in the expression of all parameters determined, namely cell number, actin stress fibers, cell spreading, vinculin, DNA d1, DNA d4, OC (osteocalcin) mRNA, Col-I (collagen type I) mRNA, ALP (alkaline phosphatase) mRNA, Col-I staining and ALP staining, as well as mineralisation, and a 1.3 fold increase for the parameters indicative for bone formation, namely OC mRNA, Col-I mRNA, ALP mRNA, Col-I staining and ALP staining, as well as mineralisation.

The invention claimed is:

1. An implant system in contact with a bone, the implant system comprising:
a body made of a ceramic material comprising zirconia; wherein
the body is an implant and comprises as an integral part thereof a surface region reaching from the surface of the body down to a predetermined depth,
the surface region of the body is enriched with a calcium component thereby forming a hydrophilic surface area,
the surface region reaches down to a depth of 1 μm at most,
the ceramic material in the surface region comprises a calcium containing crystalline phase, where the crystalline phase is a Ca—Zr—O containing phase, and
the hydrophilic surface area is formed at least on the portion of the body in direct contact with the bone.

2. The implant system according to claim 1, wherein the calcium component is integrated in the ceramic material of the surface region.

3. The implant system according to claim 1, wherein the calcium component is calcium ions or calcium oxide.

4. The implant system according to claim 1, wherein the proportion of the calcium component increases continuously from the predetermined depth towards the surface of the body.

5. The implant system according to claim 1, wherein the hydrophilic surface area is defined by a contact angle of less than 90°.

6. The implant system according to claim 1, wherein the hydrophilic surface area is formed on the entire surface of the body.

7. The implant system according to claim 1, wherein the ceramic material comprises yttria-stabilized zirconia.

8. The implant system according to claim 1, wherein the Ca—Zr—O containing phase is selected from the group consisting of: a CaO—$ZrO_2$ phase, a monoclinic $CaZr_4O_9$ phase, a cubic $CaZrO_3$ phase, and an orthorhombic $CaZrO_3$ phase.

9. The implant system according to claim 1, wherein at least a part of the hydrophilic surface area has a surface roughness obtainable by a surface roughness treatment, said surface roughness being increased with respect to a non-treated surface area of the hydrophilic surface area.

10. The implant system according to claim 1, wherein
the implant system is a one-part dental implant system, and
the implant is a dental implant.

11. The implant system according to claim 1, wherein
the implant is a dental implant, and
the implant system is a two-part dental implant system that further comprises an abutment for the dental implant.

12. The implant system according to claim 1, wherein
the implant system is a one-part dental implant system, and
the implant is a dental implant comprising:
an anchoring part configured to be anchored in the bone, and
a mounting part configured to be a base for the direct or indirect attachment of a suprastructure selected from the group consisting of a crown or a bridge.

13. The implant system according to claim 1, wherein
the implant system is a two-part dental implant system;
the implant is a dental implant; and
the two-part dental implant system further comprises an abutment configured to serve as mounting part for the dental implant and serves to connect the dental implant that is anchored in the bone to a suprastructure selected from the group consisting of a crown or a bridge;
wherein
the abutment is made of a ceramic material comprising zirconia,
the abutment comprising as an integral part thereof a surface region reaching from the surface of the abutment down to a predetermined depth, wherein
the surface region of the abutment is enriched with a calcium component thereby forming a hydrophilic surface area,
the surface region reaches down to a depth of 1 μm at most, and the ceramic material in the surface region comprises a calcium containing crystalline phase, where the crystalline phase is a Ca—Zr—O containing phase.

14. The implant system according to claim 1, wherein the surface region reaches down to a depth of 500 nm at most.

15. The implant system according to claim 1, wherein the surface region reaches down to a depth of 200 nm at most.

16. The implant system according to claim 1, wherein the hydrophilic surface area is defined by a contact angle of less than 30°.

17. The implant system according to claim 1, wherein the hydrophilic surface area is defined by a contact angle of less than 10°.

18. An implant system in contact with a soft tissue, the implant system comprising:
 a body made of a ceramic material comprising zirconia; wherein
  the body is an implant and comprises as an integral part thereof a surface region reaching from the surface of the body down to a predetermined depth,
  the surface region of the body is enriched with a calcium component thereby forming a hydrophilic surface area,
  the surface region reaches down to a depth of 1 μm at most,
  the ceramic material in the surface region comprises a calcium containing crystalline phase, where the crystalline phase is a Ca—Zr—O containing and
  the hydrophilic surface area is formed at least on the portion of the body in direct contact with the soft tissue.

19. The implant system according to claim 18, wherein the hydrophilic surface area is formed on the entire surface of the body.

20. The implant system according to claim 18, wherein the surface region reaches down to a depth of 500 nm at most.

21. The implant system according to claim 18, wherein the hydrophilic surface area is defined by a contact angle of less than 90°.

22. The implant system according to claim 18, wherein
 the implant system is a two-part dental implant system;
 the implant is a dental implant; and
 the two-part dental implant system further comprises an abutment configured to serve as mounting part for the dental implant and serves to connect the dental implant that is anchored in a bone to a suprastructure selected from the group consisting of a crown or a bridge; wherein
  the abutment is made of a ceramic material comprising zirconia,
  the abutment comprising as an integral part thereof a surface region reaching from the surface of the abutment down to a predetermined depth, wherein
  the surface region of the abutment is enriched with a calcium component thereby forming a hydrophilic surface area,
  the surface region reaches down to a depth of 1 μm at most, and
  the ceramic material in the surface region comprises a calcium containing crystalline phase, where the crystalline phase is a Ca—Zr—O containing phase.

* * * * *